(12) United States Patent
King

(10) Patent No.: US 8,182,547 B2
(45) Date of Patent: May 22, 2012

(54) NEGATIVE GAUGE PRESSURE MOISTURE MANAGEMENT AND SECURE ADHERENCE ARTIFICIAL LIMB SYSTEM AND ASSOCIATED METHODS

(76) Inventor: Charles King, Cumberland, MD (US)

(*) Notice: Subject to any disclaimer, the term of this patent is extended or adjusted under 35 U.S.C. 154(b) by 153 days.

(21) Appl. No.: 12/618,163

(22) Filed: Nov. 13, 2009

(65) Prior Publication Data

US 2010/0125342 A1    May 20, 2010

Related U.S. Application Data

(63) Continuation-in-part of application No. 11/518,064, filed on Sep. 8, 2006, now abandoned.

(60) Provisional application No. 61/199,248, filed on Nov. 14, 2008, provisional application No. 60/715,313, filed on Sep. 8, 2005, provisional application No. 60/724,512, filed on Oct. 8, 2005, provisional application No. 60/749,942, filed on Dec. 12, 2005, provisional application No. 60/759,327, filed on Jan. 14, 2006, provisional application No. 60/760,074, filed on Jan. 18, 2006, provisional application No. 60/760,596, filed on Jan. 21, 2006, provisional application No. 60/777,240, filed on Feb. 27, 2006, provisional application No. 60/798,533, filed on May 8, 2006, provisional application No. 60/833,368, filed on Jul. 26, 2006, provisional application No. 60/837,805, filed on Aug. 14, 2006.

(51) Int. Cl.
*A61F 2/80* (2006.01)

(52) U.S. Cl. .......................................... 623/34

(58) Field of Classification Search ............... 623/33–38
See application file for complete search history.

(56) References Cited

U.S. PATENT DOCUMENTS

| 2,834,025 | A |   | 5/1958 | Leavy ................................. 3/17 |
| 3,377,416 | A |   | 4/1968 | Kandel ........................ 264/222 |
| 4,917,795 | A |   | 4/1990 | Sable et al. .................. 210/120 |
| 5,258,037 | A |   | 11/1993 | Caspers .......................... 623/36 |
| 5,411,321 | A |   | 5/1995 | Harness ........................... 303/7 |
| 5,466,261 | A |   | 11/1995 | Richelsoph ..................... 623/16 |
| 5,480,455 | A |   | 1/1996 | Norvell ........................... 623/36 |
| 5,571,208 | A |   | 11/1996 | Caspers .......................... 623/32 |
| 5,658,353 | A | * | 8/1997 | Layton ........................... 623/34 |
| 5,728,169 | A |   | 3/1998 | Norvell ........................... 623/36 |
| 5,888,230 | A |   | 3/1999 | Helmy ............................ 623/34 |

(Continued)

OTHER PUBLICATIONS

Board et al., Department of Health, St. Cloud State University, Minnesota, USA; "A Comparison of Trans-Tibial Amputee Suction and Vacuum Socket Conditions", pp. 202-208, 2001.

*Primary Examiner* — Bruce E Snow
(74) *Attorney, Agent, or Firm* — Allen, Dyer, Doppelt, Milbrath & Gilchrist, P.A.

(57) ABSTRACT

The negative gauge pressure moisture management and secure adherence artificial limb system is to be attached to a residual limb of an amputee. The artificial limb system includes a negative gauge pressure airflow liner, a surface area multiplying textile layer with a proximal airflow seal to surround at least a portion of the residual limb and define a regulated negative gauge pressure environment between the residual limb and the negative gauge pressure liner. The liner has a plurality of airflow passageways defining inflow air channels and an outflow air channel in fluid communication with the defined regulated negative gauge pressure environment. An airflow control system is connected inline with the outflow and inflow air channels. The airflow control system includes an airflow regulation device and an airflow initiating device.

29 Claims, 10 Drawing Sheets

U.S. PATENT DOCUMENTS

| | | | |
|---|---|---|---|
| 6,014,823 A | 1/2000 | Lakic | 36/93 |
| 6,231,616 B1 | 5/2001 | Helmy | 623/34 |
| 6,508,842 B1 | 1/2003 | Caspers | 623/32 |
| 6,544,292 B1 | 4/2003 | Laghi | 623/36 |
| 6,554,868 B1 | 4/2003 | Caspers | 623/34 |
| 6,645,253 B2 | 11/2003 | Caspers | 623/26 |
| 6,726,726 B2 | 4/2004 | Caspers | 623/34 |
| 6,761,742 B2 | 7/2004 | Caspers | 623/34 |
| 6,974,484 B2 | 12/2005 | Caspers | 623/34 |
| 2001/0016781 A1 | 8/2001 | Caspers | 623/34 |
| 2002/0091449 A1 | 7/2002 | Caspers et al. | 623/34 |
| 2003/0181990 A1 | 9/2003 | Phillips | 623/37 |
| 2004/0030411 A1 | 2/2004 | Caspers | 623/37 |
| 2004/0163278 A1 | 8/2004 | Caspers et al. | 36/3 |
| 2004/0167447 A1 | 8/2004 | Johnson, III | 602/5 |
| 2004/0167638 A1 | 8/2004 | Caspers | 623/27 |
| 2005/0131549 A1 | 6/2005 | Caspers | 623/34 |
| 2005/0197611 A1 | 9/2005 | Taranow | 602/62 |

* cited by examiner

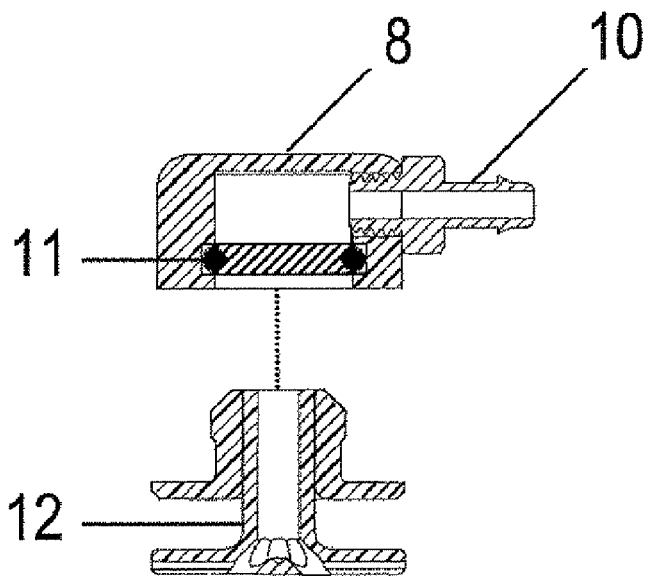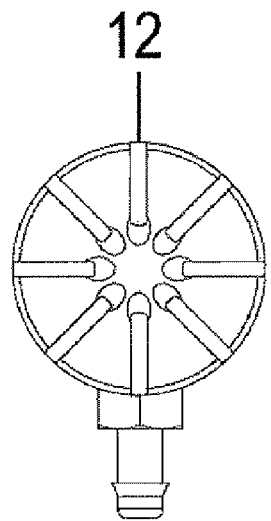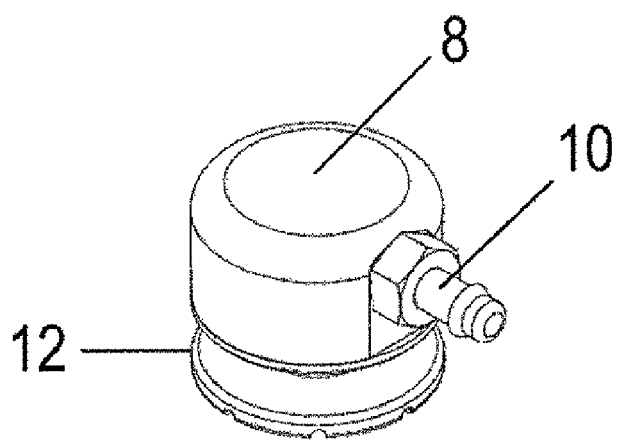

NEGATIVE GAUGE PRESSURE MOISTURE MANAGEMENT AND SECURE ADHERENCE ARTIFICIAL LIMB SYSTEM AND ASSOCIATED METHODS

RELATED APPLICATIONS

This application claims the benefit of 61/199,248 filed Nov. 14, 2008 and is a Continuation-in-Part (CIP) application of U.S. patent application Ser. No. 11/518,064 filed Sep. 8, 2006 now abandoned, the entire disclosure of which is incorporated herein by reference, and which claims the benefit of U.S. Provisional Application Nos. 60/715,313 filed Sep. 8, 2005, 60/724,512 filed Oct. 8, 2005, 60/749,942 filed Dec. 12, 2005, 60/759,327 filed Jan. 14, 2006, 60/760,074 filed Jan. 18, 2006, 60/760,596 filed Jan. 21, 2006, 60/777,240 filed Feb. 27, 2006, 60/798,533 filed May 8, 2006, 60/833,368 filed Jul. 26, 2006, 60/837,805 filed Aug. 14, 2006 all of which are hereby incorporated herein in their entireties by reference.

FIELD OF THE INVENTION

The present invention relates to the field of artificial limbs, and, more particularly, to liners employed in artificial limbs, related systems and related methods.

BACKGROUND OF THE INVENTION

Excessive perspiration is a problem encountered by the amputee population wearing an artificial limb and liner. The liner, which is donned upon the residual limb of the amputee, for both suspension and comfort, can be described as a nonporous elastomeric material with high thermal insulation properties nearly impermeable to moisture, for example, as discussed in the article by Hachisuka et al. (2001) entitled "Moisture permeability of the total surface bearing prosthetic socket with a silicone liner: is it superior to the patella-tendon bearing prosthetic socket?" J. Uoeh, 23, 225-32. An artificial limb liner seals off airflow to the residual limb, which results in an accumulation of sensible and insensible perspiration between the liner and limb.

Accumulation of perspiration adversely affects limb health. Skin irritation and problems such as dermatitis and infection are clinically relevant issues that have long been known to be fostered under moist conditions (e.g. see the article to Barnes (1956) entitled "Skin health and stump hygiene". Artif Limbs, 3, 4-19); particularly if the liner and residual limb are not cleaned appropriately or frequently. The accumulated perspiration decreases the friction suspending the liner on the residual limb. This can cause a pistoning action, which describes the relative movement between the residual limb and liner.

Excessive limb pistoning leads to friction-related injuries and skin irritation. Examples of such problems are discussed in: Naylor, P. F. (1955) "The skin surface and friction", Br J Dermatol, 67, 239-46; Naylor, P. F. D. (1955) "Experimental friction blisters", Br J Dermatol, 67, 327-342; and Akers et al. (1972) "The friction blister", Military Medicine, 137, 1-7. Such pistoning of the residual limb and artificial limb liner creates the potential for catastrophic failure of the suspension of the limb.

Amputees often complain about the accumulation of perspiration and for good reason. While a few artificial limb users' sweat glands may reduce secretions over time, such a response is neither common nor consistent among all users. To prevent skin problems and to maintain secure adherence, moisture accumulation is currently managed by the amputees themselves. They regularly remove their prosthesis to empty accumulated moisture and dry their limb. An artificial limb system that removes accumulated perspiration would alleviate the conditions that make the skin more susceptible to injuries while achieving a lasting secure adherence. It might also improve their quality of life. A survey of lower limb amputees (n=90) found that perspiration inside the prosthesis was one of the five most common reason for a reduced quality of life during the summer months, as discussed in Hagberg et al. (2001) "Consequences of non-vascular trans-femoral amputation: a survey of quality of life, prosthetic use and problems", Prosthet Orthot Int, 25, 186-94.

The current state of technology relative to moisture management in a modern artificial limb is fundamentally lacking. An artificial limb liner is donned on the amputee's stump creating an airtight seal from which the artificial limb is suspended. Sensible and insensible perspiration is trapped between the residual limb and liner in this sealed system until a build-up of moisture necessitates complete removal and "airing" of the stump.

There is a need for an approach to reduce perspiration build up in a suspension and comfort liner used in an artificial limb. The approach should also improve secure adherence by limiting relative motion between the liner and residual limb and thus mitigate pistoning.

SUMMARY OF THE INVENTION

In view of the foregoing background, it is therefore an object of the present invention to provide an artificial limb system and method to manage perspiration accumulation, improve suspension and provide both apparent and actual cooling to the residual limb of an amputee.

This and other objects, features, and advantages in accordance with the present invention may be provided by an negative gauge pressure moisture management and secure adherence artificial limb system to be attached to a residual limb of an amputee. The system includes a negative gauge pressure airflow liner, a surface area multiplying textile layer with an airflow seal to surround at least a portion of the residual limb and define a regulated negative gauge pressure environment between the residual limb and the airflow liner. The liner has a plurality of airflow passageways defining the inflow air channels and outflow air channel in fluid communication with the defined regulated negative gauge pressure environment. An airflow control system is connected inline with the outflow and inflow air channels. The airflow control system comprises an airflow regulation device and an airflow initiating device.

The plurality of passageways of the airflow liner includes the inflow air channels in fluid communication with the regulated negative gauge pressure environment and an outflow air channel in fluid communication with the regulated negative gauge pressure environment. The air inflow channels include quick detachable air inflow channel ports which are located on the proximal aspect of the artificial limb airflow liner. These inflow channel ports have an occlusion preventing airflow flange design, which comprises a plurality of airflow holes in a circular pattern, angled such that they feed distally into a central inflow air channel and proximally into airflow grooves along the face of the flange. The air outflow channel includes a distal air outflow channel port located at the distal end of the artificial limb liner. It also has an occlusion preventing airflow flange that has a plurality of airflow holes in a circular pattern, angled such that they feed into a central outflow air channel distally and proximally into airflow grooves along the face of the flange.

An airflow control system is connected inline with the outflow and inflow air channels. The airflow control system comprises an airflow regulation device and an airflow initiating device. An airflow regulation device may be connected at least to the outlet port, and may include an electric negative gauge pressure generating device connected to the outlet port, and an associated control circuit. An airflow initiating device may be connected at least to the inlet port, and may include an electromechanical airflow proportioning mechanism and associated control circuit.

The airflow control system may also include a battery to power the negative gauge pressure device with control circuit and electromechanical airflow proportioning mechanism with control circuit, and an enclosure may contain the battery, negative gauge pressure device with control circuit and electromechanical airflow proportioning mechanism with associated control circuit. A radio transmitter may be included for activating the electromechanical airflow proportioning mechanism.

Objects, features, and advantages in accordance with the present invention may be provided by a negative gauge pressure moisture management and secure adherence artificial limb system to be attached to a residual limb of an amputee, wherein the system includes a negative gauge pressure airflow liner, and a surface area multiplying textile layer with an airflow seal to define a regulated negative gauge pressure environment between the airflow liner and the residual limb. The liner has a plurality of airflow passageways defining the inflow air channels and outflow air channel, in fluid communication with the regulated negative gauge pressure environment. The air inflow channels may include quick detachable inflow channel ports which are placed in the proximal aspect of the artificial limb liner.

The inflow channel ports may have an occlusion preventing flange design, which comprises a plurality of airflow holes in a circular pattern, angled such that they feed into a central inflow air channel distally and proximally into airflow grooves along the face of the flange. The air outflow channel includes a outflow channel port located at the distal end of the artificial limb liner. It also has an occlusion preventing airflow flange that has a plurality of airflow holes in a circular pattern, angled such that they feed into a central outflow air channel distally and proximally into airflow grooves along the face of the flange. An airflow control system is connected inline with the outflow and inflow air channels. The airflow control system comprises an airflow regulation device and an airflow initiating device. The airflow regulation device is connected to the outflow channel and may include an electric negative gauge pressure generating device and associated circuit controller. The airflow initiating device is connected to the inflow air channel and may include an electromechanical airflow proportioning mechanism and control circuit, which may be user activated by radio link.

Objects, features, and advantages in accordance with the present invention may also be provided by a method of attaching an artificial limb to a residual limb. The method includes providing a negative gauge pressure airflow liner, providing a surface area multiplying textile layer with an airflow seal to surround at least a portion of the residual limb and define a regulated negative gauge pressure environment between the negative gauge pressure airflow liner and the residual limb. The liner has a plurality of airflow passageways therethrough defining the inflow air channels and outflow air channel in fluid communication with the regulated negative gauge pressure environment. The method includes providing an airflow control system connected inline with the outflow and inflow air channels. The airflow control system comprises an airflow regulation device and an airflow initiating device.

The liner has a plurality of airflow passageways defining the inflow air channels and outflow air channel, in fluid communication with the regulated negative gauge pressure environment. The air inflow channels include quick detachable air inflow channel ports which are placed in the proximal aspect of the artificial limb liner. These inflow channel ports have an occlusion preventing airflow flange design, which comprises a plurality of airflow holes in a circular pattern, angled such that they feed into a central inflow air channel distally and proximally into airflow grooves along the face of the flange. The air outflow channel includes a distal air outflow channel port located at the distal end of the artificial limb liner. It also has an occlusion preventing airflow flange that has a plurality of airflow holes in a circular pattern, angled such that they feed into a central outflow air channel distally and proximally into airflow grooves along the face of the flange.

An airflow control system is connected between the inflow and outflow channels. The negative gauge pressure regulation device is connected to the outflow channel and may include an electric negative gauge pressure generating device and circuit controller. An airflow initiating device is connected to the inflow air channel and may include an electromechanical airflow proportioning mechanism with associated circuit controller.

The airflow control system further comprises: a battery to power the electric negative gauge pressure generating device with circuit controller and electromechanical airflow proportioning mechanism with associated controller and radio link; and a enclosure containing the battery, electric negative gauge pressure generating device with controller and electromechanical airflow proportioning mechanism with controller and radio link.

The many embodiments of the present invention described herein contribute to perspiration moisture management, improving suspension by limiting pistoning between the residual limb and liner and providing both apparent and actual cooling of the residual limb.

BRIEF DESCRIPTION OF THE DRAWINGS

FIGS. 4A-4C are schematic perspective, expanded cross-sectional and bottom views of the proximal air inflow port with its occlusion preventing flange, a feature of the airflow artificial limb liner to be attached to a residual limb in accordance with the present invention.

DETAILED DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. The dimensions of layers and regions may be exaggerated in the figures for greater clarity.

Figure 1:
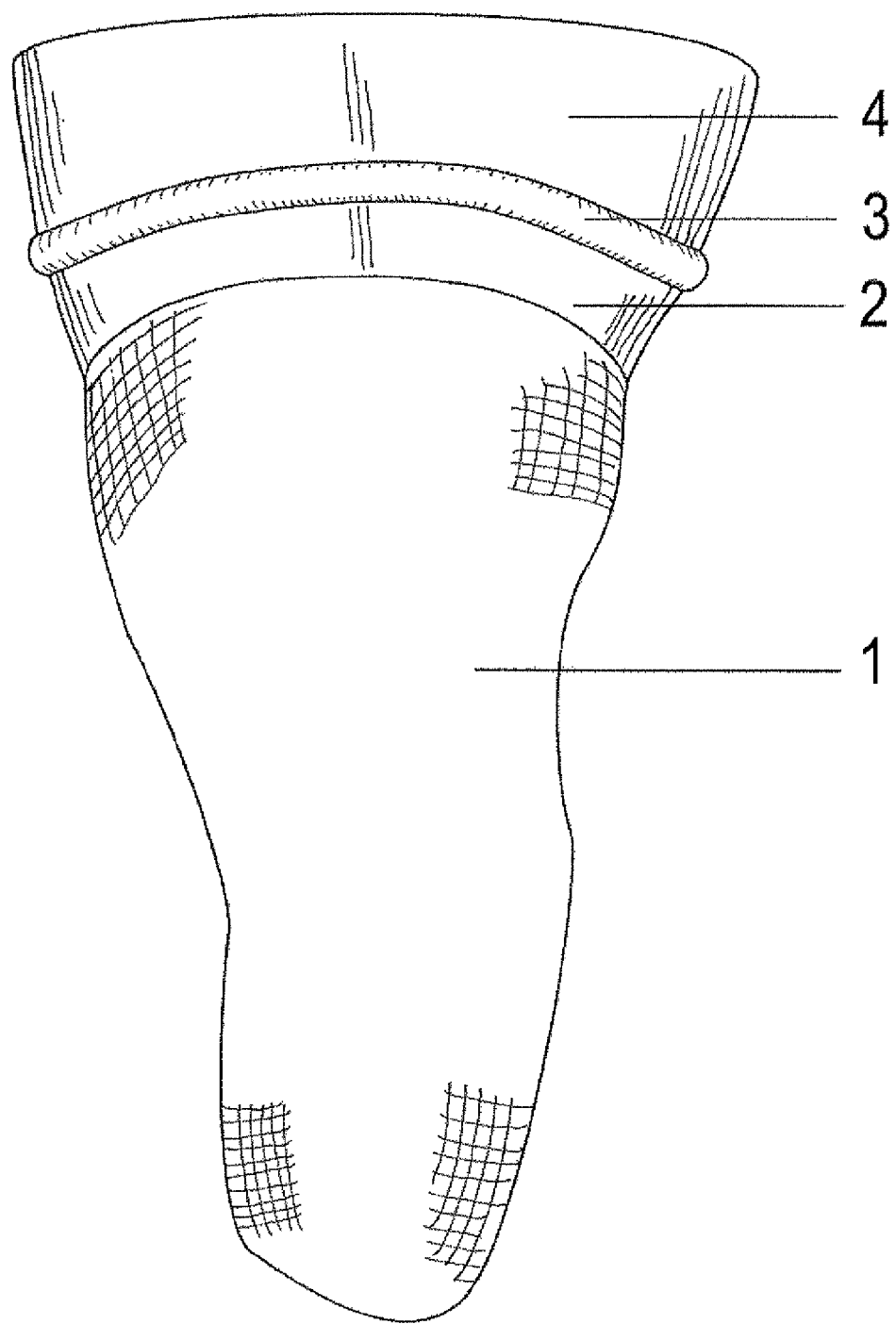
FIG. 1 is a schematic view of the surface area multiplying textile layer with proximal airflow seal to be attached to a residual limb in accordance with the present invention.

Referring initially to FIG. 1, the surface area multiplying textile layer 1 with airflow seal 4 will now be described. A textile layer 1, which conforms snugly to the shape of an amputee's stump is laminated with a flexible elastomeric top 4 (e.g. silicone), of such a diameter as to conform comfortably and snugly with the proximal region of an amputee's residuum. The textile layer 1 is donned directly on the amputee's stump and worn underneath the negative gauge pressure airflow liner (described below). The textile layer 1 surrounds at least a portion of the residual limb and defines a regulated negative gauge pressure environment between negative gauge pressure airflow liner and the residual limb. Increasing the surface area facilitates transpiration, evaporation, and transporting moisture. The airflow seal 4 of the surface area multiplying textile layer 1 includes a gently tapered laminate transition area 2, where the fibers of the textile are adherently intertwined with silicone and terminate at the raised annular ring 3. The annular ring 3 and proximal seal area 4 are devoid of textile fibers, which effectively seals both pressure and airflow. As such, the airflow seal 4 is preferably an impervious seal.

An alternate embodiment of the surface area multiplying textile layer 1 with airflow seal 4 may contain defined airflow passages incorporated in the proximal seal area 4 and in fluid communication with the surface area multiplying textile layer. A further embodiment may include multiple annular rings varying in shape and placement on the airflow seal 4.

Figure 2:
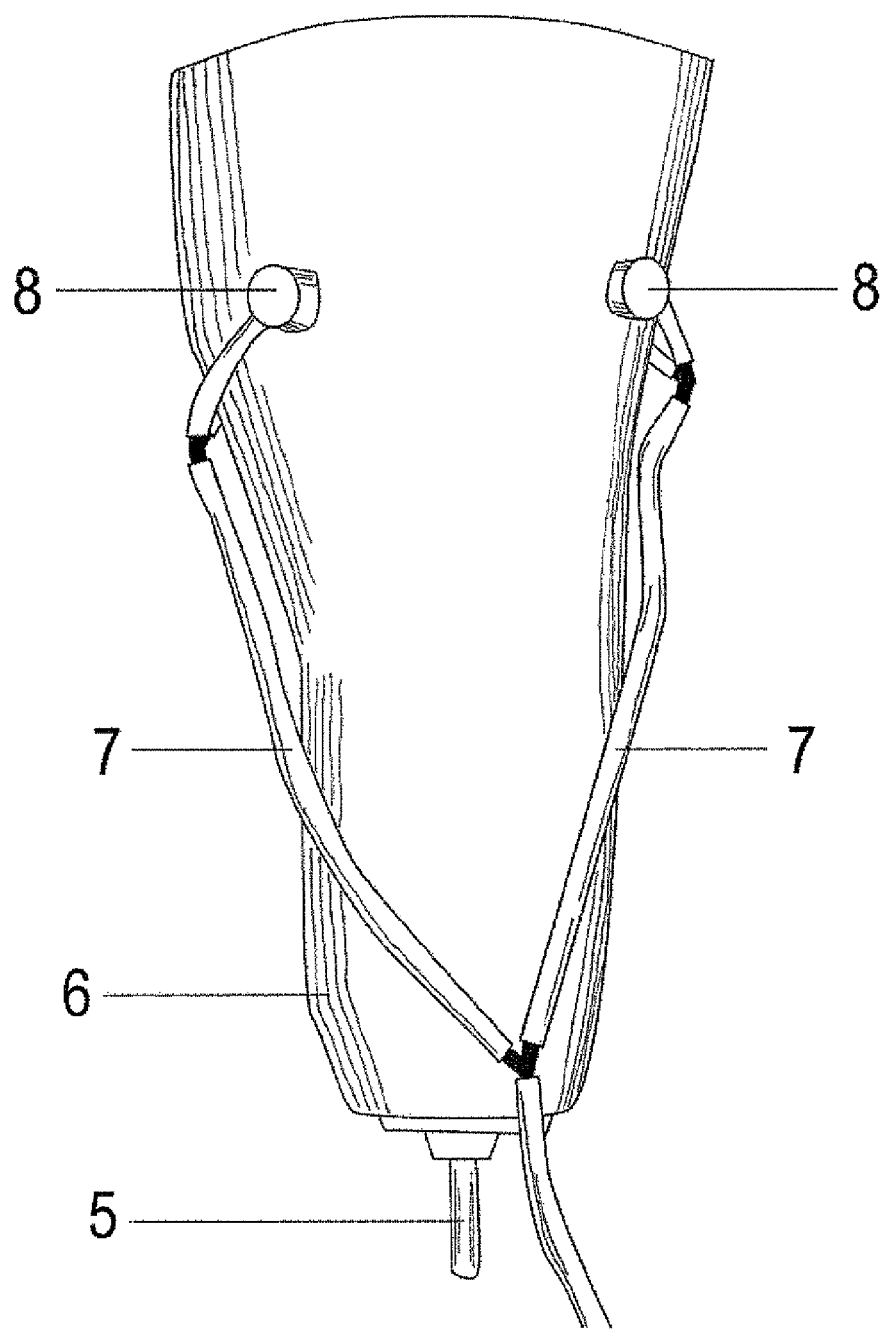
FIG. 2 is an anterior view of the airflow artificial limb liner to be attached to a residual limb in accordance with the present invention.

Referring to FIG. 2, the negative gauge pressure airflow liner 6 will be described. It is donned over the surface area multiplying textile layer 1 with airflow seal 4 depicted in FIG. 1. With the application of negative gauge pressure, the residual limb and liner 6 are drawn into secure adherence via the fluid communication action of the surface area multiplying textile layer 1 with airflow seal 4. The airflow liner 6 for artificial limbs includes an elastomeric tubular body and includes proximal inflow air channels 7 and at least one distal outflow air channel 5 (hollow locking suspension pin). In view of the secure adherence, and elastomeric tubular body, the airflow liner 6 may define an artificial limb-conforming flexible airflow liner.

The inflow air channels 7 may further include quick detachable inflow channel ports and associated removable air channel caps 8. Negative gauge pressure (vacuum) is commonly expressed in inches of mercury ("Hg) or millimeters of mercury (mmHg) which is equal to torr. One atmosphere equals 14.7 psia (0 psig), 29.92"Hg (0"Hg absolute), 760 mmHg, 760 torr or 1,013 mbar.

An alternate embodiment of the airflow liner 6 design may have a plurality of holes in the proximal aspect of the artificial limb liner. The holes are shaped in a conical fashion with the smallest part of the cone on the inside of the liner and the largest on the outside. These holes cover a similar series of perforations in the proximal part of the airflow seal of the surface area multiplying textile layer and moisture is effectively transported to the surface of the artificial limb liner and away from the skin of the amputee.

Figure 3:
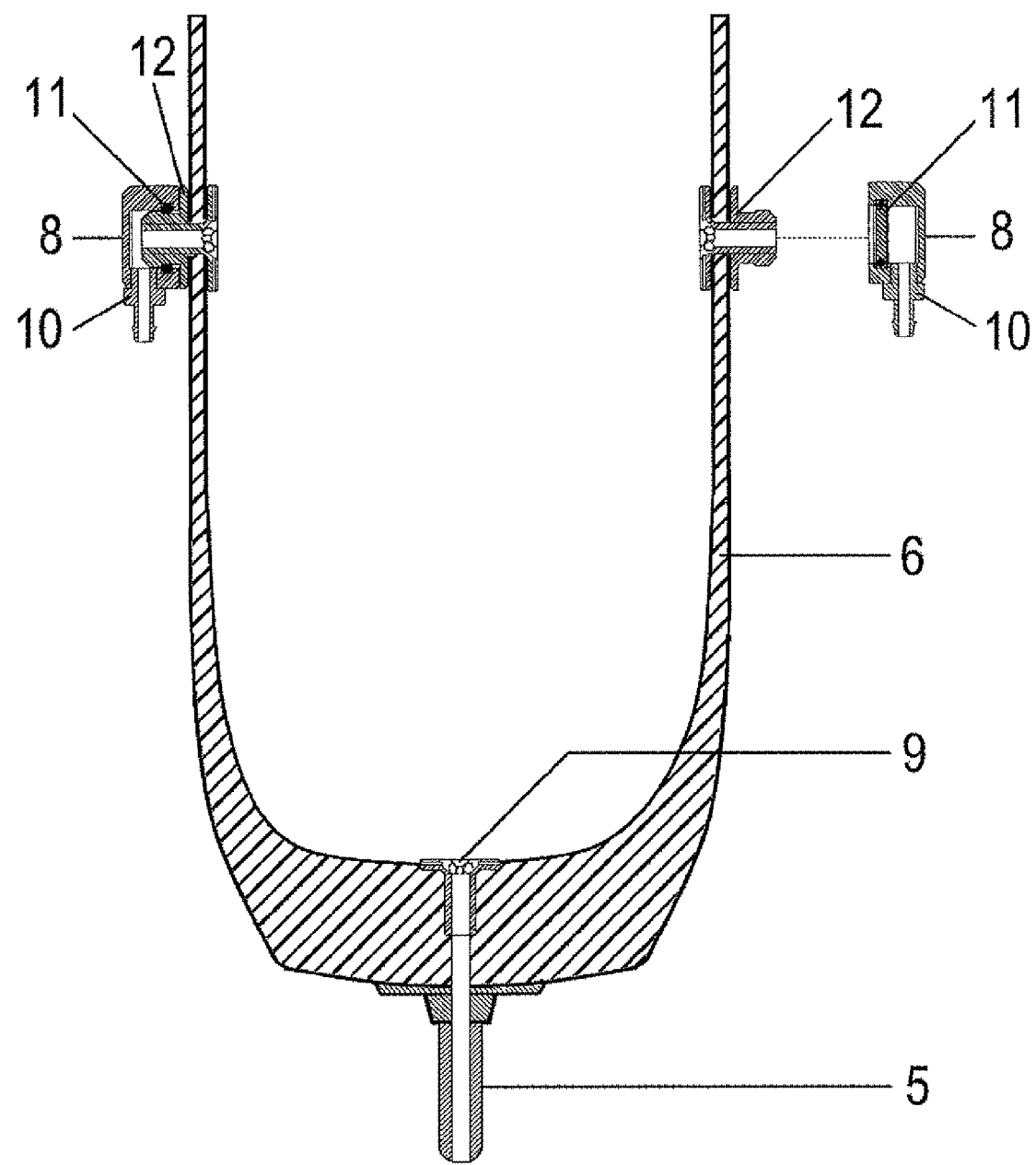
FIG. 3 is a schematic cross-sectional view of the airflow artificial limb liner to be attached to a residual limb in accordance with the present invention.

Referring now to FIG. 3, a cross-section of the negative gauge pressure airflow liner 6, the air channel caps are shown as proximal quick detachable air channel inflow ports with occlusion preventing flanges 12, with sealing O-ring 11, and barb fitting 10. Also depicted is the distal air outflow port 5 (or hollow locking pin) and including occlusion preventing flange 9.

Referring to FIGS. 4A-4C, depicted are different views of the proximal quick detachable air inflow channel ports 8 with occlusion preventing flange 12. The air inflow channel extends through the flange 12 and ports or removable channel caps 8 with sealing O-ring 11, and barb fitting 10. The bottom view (FIG. 4C) of the occlusion preventing flange 12 depicts its plurality of airflow holes in a circular pattern, angled such that they feed into a central inflow air channel distally and proximally into airflow grooves along the face of the flange. This design prevents the surface multiplying textile layer 1 from occluding the airflow passageways under negative gauge pressure. This design also protects the skin of the amputee from localized negative gauge pressures.

An alternate embodiment for the proximal air inflow port would involve a 360° annular airflow port molded in the artificial limb liner. A port encompassing 360° of equal air distribution would be advantageous in removing moisture from the system efficiently. It would contain a plurality of airflow holes of varying sized diameters to balance airflow equally around the limb.

Figures 5A, 5B, 5C:
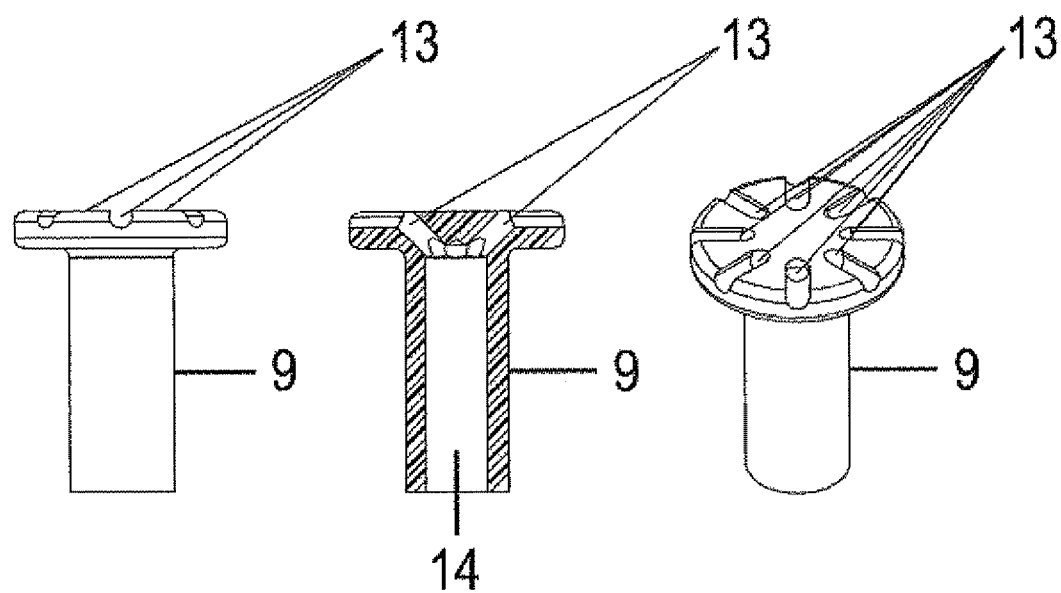
FIGS. 5A-5C are schematic side, cross-sectional and perspective views of the distal air outflow port with an occlusion preventing flange, a feature of the airflow artificial limb liner to be attached to a residual limb in accordance with the present invention.

Referring to FIGS. 5A-5C, the distal air outflow port 5 with occlusion preventing flange 9 will be described. The port 5 has a plurality of airflow holes or channels 13 in a circular pattern, angled such that they feed into a central outflow air channel distally 14 and proximally into airflow grooves along the face of the flange. This design prevents the surface multiplying textile layer 1 from occluding the airflow passageways. This design also protects the skin of the amputee from localized negative gauge pressures.

Figure 6A:
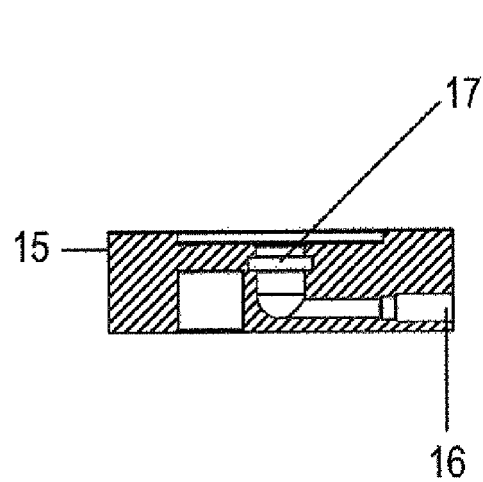
FIGS. 6A and 6B are schematic cross-sectional and perspective views of the 4 bolt airflow lamination plate for fabrication in an artificial limb to be attached to a residual limb in accordance with the present invention.
Figure 6B:
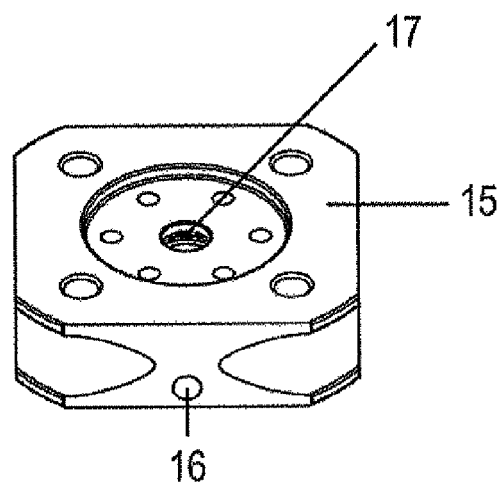

Referring to FIGS. 6A and 6B, depicted is a four-bolt airflow lamination plate 15. A pin locking mechanism is secured to the four-bolt plate and a hollow locking pin (e.g. as shown in FIG. 3) passes through the locking mechanism and seals against the O-ring 17 retained in the four-bolt plate 15. The outflow airflow channel exits the artificial limb socket past a threaded section 16, to receive a barb fitting.

Figure 7:
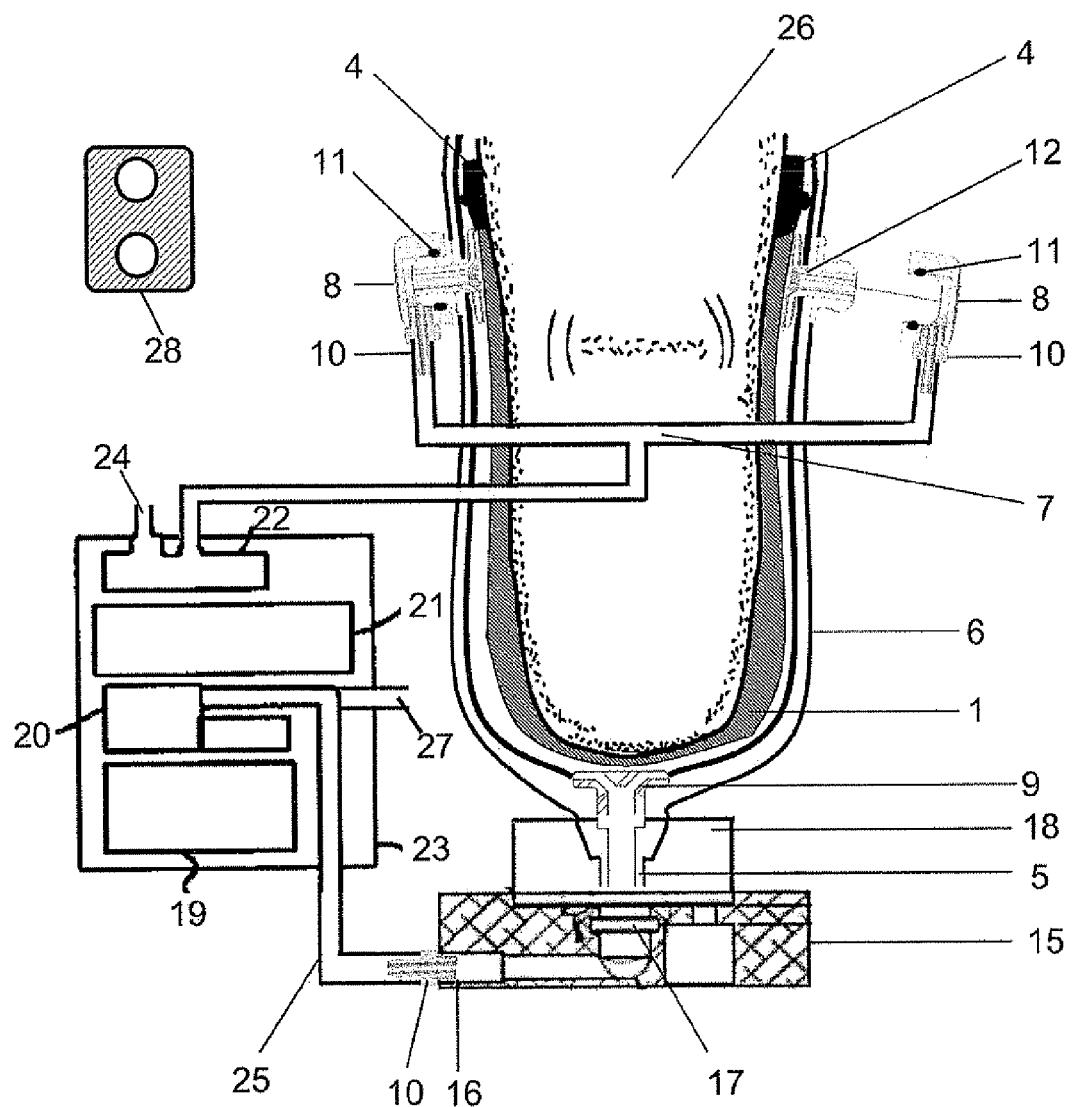
FIG. 7 is a schematic diagram of the surface area multiplying textile layer with airflow seal, the negative gauge pressure airflow liner on a residual limb of an amputee and airflow control system in accordance with the present invention.

Referring to FIG. 7, which depicts a schematic cutaway of the surface area multiplying textile layer 1 with airflow seal 4 and the negative gauge pressure airflow liner 6 on a residual limb 26 of an amputee. Airflow passageways are defined by the inflow air channels 7 and outflow air channel 25 which are in fluid communication with the regulated negative gauge pressure environment between the airflow liner 6, the residual limb of the amputee 26, and the surface area multiplying textile layer 1 with proximal airflow seal 4. The inflow air channel 7 and the outflow air channel 25 connect to the airflow control system 23.

The airflow control system 23 includes the negative gauge pressure generating device 20 and circuit controller 19 (which are described together as the airflow regulation device 51, described below with reference to FIG. 8) and the key fob radio link 28 operated electromechanical airflow proportioning mechanism 22 and circuit controller 21 (which are described together as the airflow initiating device 52, described below with reference to FIG. 9).

The airflow regulation device 51 creates and maintains a small pressure differential between the residual limb 26 and the artificial limb airflow liner 6. When the artificial limb user actuates the electromechanical proportioning mechanism (e.g. through depressing the key fob 28, or a pushbutton on the control circuit 21) environmental air is drawn into the airflow passageways at point 24 through the air channels 7, through the barb fitting 10, through the quick detachable air channel ports and removable channel caps 8, with an O-ring seal 11 through the proximal air inflow ports with occlusion preventing flanges 12, through the surface multiplying textile layer 1, where the air is then passed along the skin surface, facilitating moisture removal and evaporation, and on to the distal air outflow port 5 with occlusion preventing flange 9. Air passes through air outflow port or channel 5 (hollow locking pin) which is securely engaged in its locking mechanism 18, and seals against the O-ring 17 retained in the four-bolt plate airflow lamination plate 15, exiting the artificial limb socket just past a threaded section 16 which has received a barb fitting 29.

The now moisture-laden air, and if the activity level is high enough, perspiration itself, passes through outflow air channel 25, to the negative gauge pressure generating device 20, and expelled at exit point 27. This humidity reducing/perspiration removal system removes sweat while maintaining a secure adherence. Although a below knee residual limb is represented in FIG. 7, this artificial limb design can be used on above knee, below knee and upper extremity amputees, as would be appreciated by those skilled in the art.

The minimal amount of negative pressure to hold the airflow liner on is a function of the weight of the artificial limb divided by the cross-sectional area of the residual limb near the distal end. A typical transtibial amputee patient might require negative 5 kPa pressure (−0.75 psi, −38 mm Hg) to securely hold their liner and artificial limb on. The ideal maintained negative gauge pressure setting to achieve secure adherence is about double the minimal negative gauge pressure needed to securely hold the limb and liner on the amputee's limb, creating a safety factor of one or unity. In the above example, a negative gauge pressure of 10 kPa would be chosen as the negative gauge pressure level to achieve a safety factor of unity.

It should be noted that there is no increase in radial compression of the liner upon the residual limb because of the application of regulated negative gauge pressure. There is, however, an increase in intimate contact between the liner and the residual limb. It should also be noted that the application of regulated negative gauge pressure to the inside of the airflow liner does not engender edema. Again, negative gauge pressure draws the liner and the skin into secure adherence.

The importance of negative gauge pressure inside the liner 6 is that it reduces relative motion between the residual limb and liner, and maintains secure adherence in the presence of moisture. The application of negative gauge pressure inside the artificial limb liner draws the liner and the skin into secure 18 adherence. The pressure loading of the skin is transferred to the liner because relative motion has been eliminated by the addition of regulated negative gauge pressure between the stump and liner.

Creating an elevated negative gauge pressure environment between the residual limb and liner 6 may evaporate the most energetic molecules of perspiration on the residual limb. Adding a mass airflow mechanism accomplished by the negative gauge pressure device removes perspiration with increased rapidity because of the inrush of air. Negative gauge pressure, by lowering saturation vapor pressure, increases the tendency of water to overcome its surface tension and evaporate, which is an endothermic (net heat loss) reaction. The more air pulled though the liner, the more moisture removed per unit time.

Figure 8:
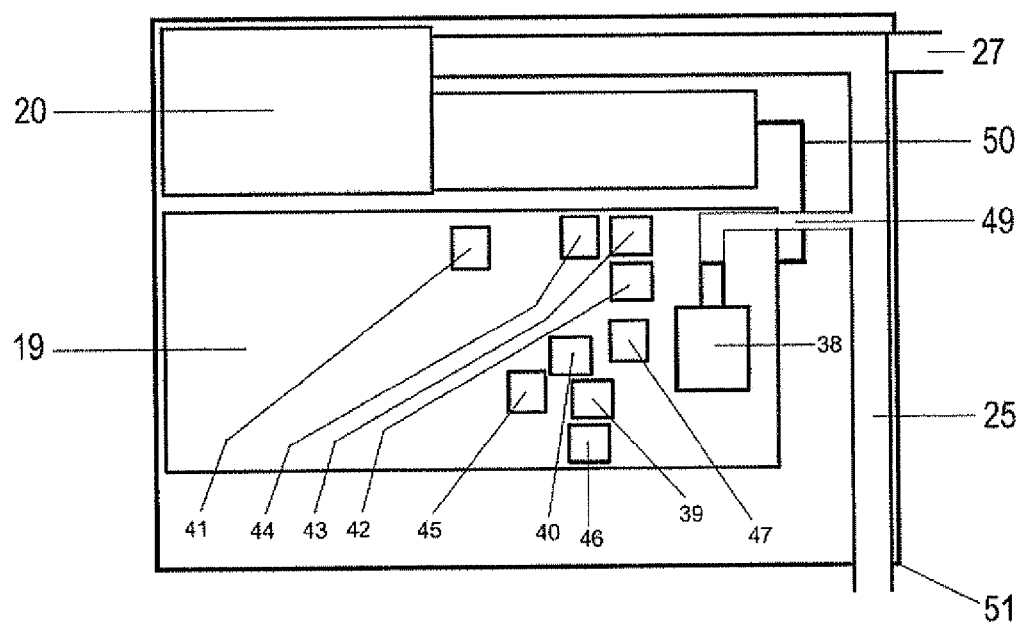
FIG. 8 is a schematic block diagram of the airflow regulation device of the airflow control system to be to used in accordance with the present invention.

Referring to FIG. 8, depicted is the airflow regulation device 51, which includes the circuit controller 19 and negative gauge pressure generating device 20. The battery powered negative gauge pressure generating device 20 is connected both electronically 50 and pneumatically 49 to the circuit controller 19.

The negative gauge pressure sensor 38 is in fluid communication at port 49 to the outflow air channel 25. Air and moisture is exhausted at exit point 27. The circuit controller 19 for the battery powered negative gauge pressure generating device 20 may include a plurality of adjustment potentiometers 39-47 that populate this analog circuit controller 19. A description of their adjustment describes features of this circuit design.

Negative Gauge Pressure Level Adjustment 39 establishes the negative gauge pressure level setting that the negative gauge pressure generating device 20 will maintain. The negative gauge pressure generating device 20 will turn on at this established setting and turn off at the established hysteresis setting. Hysteresis adjustment 40 is adjusted in a positive direction above the negative gauge pressure level adjustment 39. When hysteresis is increased, the negative gauge pressure generating device stops at a higher negative gauge pressure level and the band between this stopping point and the turn on point (established by the negative gauge pressure level adjustment 39), is the dead band or hysteresis. The advantage to this configuration is that the set hysteresis amount is consistent throughout the negative gauge pressure level adjustment range.

Regarding motor speed adjustment 41, the negative gauge pressure generating device's 20 motor speed is adjustable to minimize device noise and conserve battery life. Depending on the negative gauge pressure level setting, the device's speed can be adjusted to efficiently maintain the desired negative gauge pressure level. The motor speed adjustment 41 adjusts the default operating speed of the device.

Airflow Initiating Device Closure/Boost Threshold 42: the electromechanical airflow proportioning mechanism 22 (e.g. FIGS. 7 and 9) is closed at an established safety minimum negative gauge pressure threshold level and a motor boost threshold is established when the airflow initiating device 52 is closed. When the electromechanical airflow proportioning mechanism 22 is closed, the airflow Initiating Device Closure/Boost Threshold 42 establishes the safety boost threshold maintaining the set negative gauge pressure level. If the negative gauge pressure level drops below the safety threshold, the negative gauge generating device speed control is disabled and the device motor speed is increased in an effort to maintain minimum negative gauge pressure. If the leak is overcome by the device, and the set negative gauge pressure level is achieved, then normal device speed adjustment is re-engaged. The motor speed, however, may not be operating fast enough to maintain the set negative gauge pressure level. In response, the speed control is again disabled, and the device will again speed up. Speed is dependent on the size of the negative gauge pressure leak. If it is small, normal speed control occurs, if it is big, a faster motor speed response occurs.

Alternate negative gauge pressure level setting 43: If the electromechanical airflow proportioning mechanism 22 is opened to let air flow through the system, the alternate negative gauge pressure level adjustment 43 sets the new negative gauge pressure adjustment level. When the electromechanical airflow proportioning mechanism 22 is open, the negative gauge pressure generating device speed regulation is effectively disabled, and maximum device speed is achieved. As long as the negative gauge pressure level is maintained above the setting of the airflow initiating device closure/Boost Threshold 42, the alternate negative gauge pressure Level Setting 43 is in operation when the electromechanical airflow proportioning mechanism 22 is open.

Timing Signal Adjustment 44 adjusts the length of time that a low negative gauge pressure signal must be maintained for the electromechanical proportioning mechanism 22 to close. Span adjustment 45 allows for full scale adjustment of the negative gauge pressure level adjustment. Negative gauge pressure sensor zero adjustment 46 adjusts for irregularities in the manufacture of the pressure sensor 38. Threshold adjustment 47 accounts for variations in device head manufacture and is adjusted so that the device efficiently starts and stops smoothly.

The circuit controller 19 for the negative gauge pressure generating device 20 employs pulse width modulation as a power saving control design. Pulse width modulation in the design is independent of battery voltage fluctuations. The controller 19 also has a unique feature of regenerative feedback. It is effective when the negative gauge pressure generator is set to run slowly. Regenerative feedback allows the negative gauge pressure generator to adapt to the encountered head pressure. When the motor speed of the negative gauge pressure generator 20 is set low, the ability of the negative gauge pressure generator to overcome head pressure is reduced and regenerative feedback prevents the situation of togging or stalling. The advantage of regenerative feedback is that it allows the negative gauge pressure generator to be set at a lower device speed than would be possible without it, with the concomitant noise level reduction. With regenerative feedback, as the load gets heavier, the negative gauge pressure generator 20 responds with increased speed. The control circuit 19 of the airflow regulation device 51 features an analog design, the benefit of which is low power consumption and inherent stability and reliability of the system.

Figure 9:
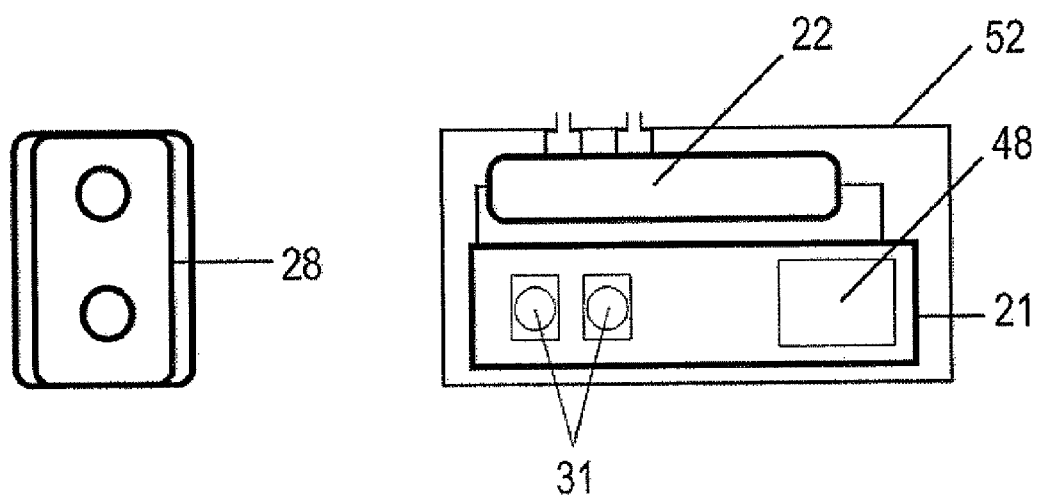
FIG. 9 is a schematic view the airflow initiating device of the airflow control system to be used in accordance with the present invention.

Referring to FIG. 9, the airflow initiating device 52 is depicted. It comprises an electromechanical airflow proportioning mechanism 22 and circuit controller 21. The electromechanical proportioning mechanism 22 is operated by key fob radio link 28 or pushbutton activation 31. The circuit controller 21 has a low voltage visual or audible indicator 48 (e.g. a beeper) to inform the user of low battery power. The controller 21 also has a low voltage closing safety feature. The electromechanical airflow proportioning mechanism 22 is closed at a set voltage level, so that the system will not be stuck open in the presence of battery failure (and no power to operate the negative gauge pressure generating device). The safety signal is continuously applied, continuously drawing battery current, locking the system closed. This allows the battery to be completely drained and not recover, so the electromechanical airflow proportioning mechanism 22 cannot be opened until a recharged or fresh battery is installed.

Figure 10:
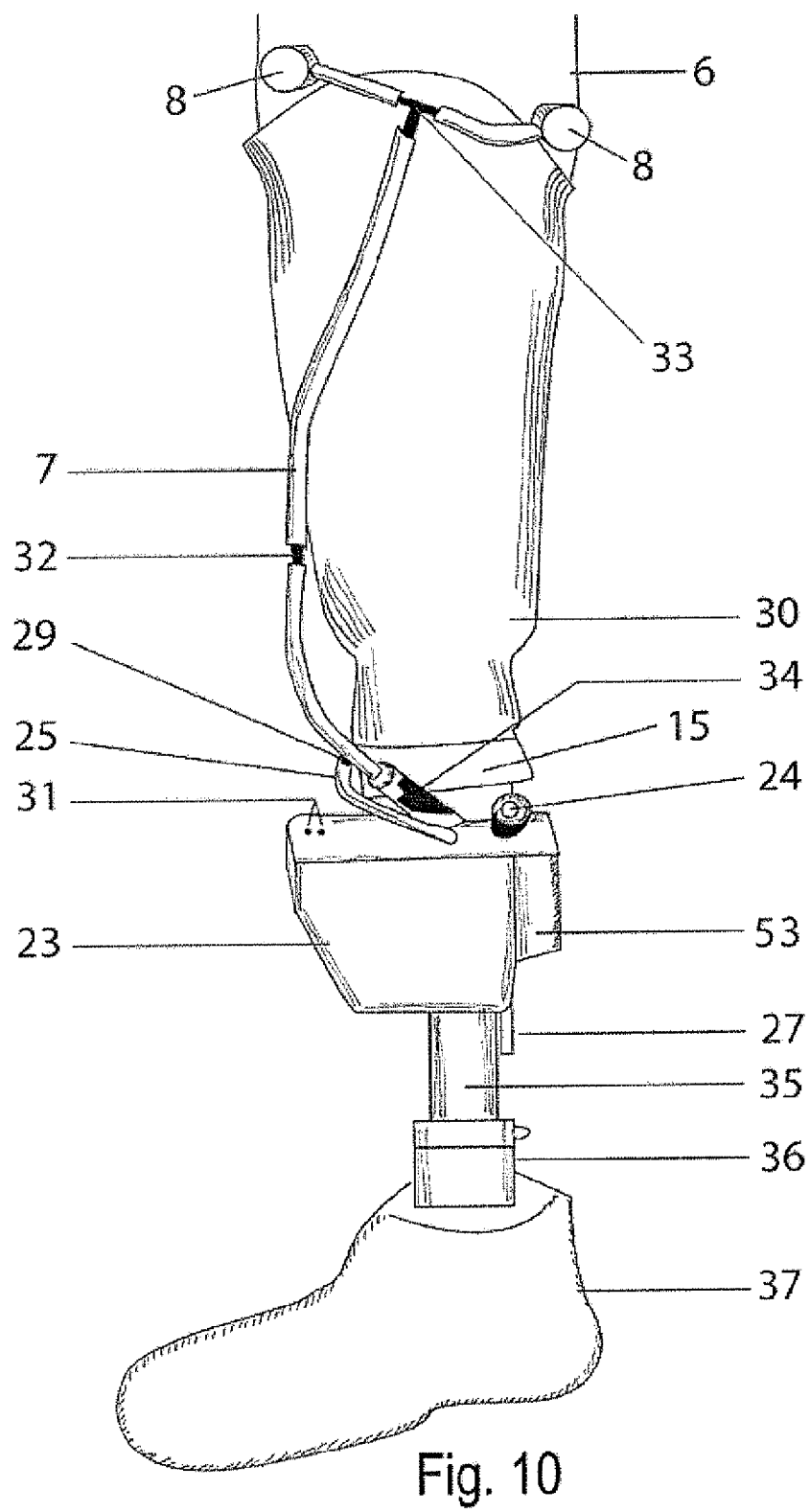
FIG. 10 is a side view of the negative gauge pressure moisture management and secure adherence artificial limb system to be attached to a residual limb in accordance with the present invention.

Referring to FIG. 10, the negative gauge pressure moisture management and secure adherence artificial limb system is depicted as reduced to practice on a residual limb of an amputee. The artificial limb comprises a rigid socket 30, attachment pylon 35, tube clamps 36 and artificial foot 37. The airflow control system 23 is attached to the pylon 35 and fits around (and obscures) the proximal tube clamp attached to the pylon 35. The inflow air channel 7, with joining Y 32 and T 33 connects distally to the airflow initiating device housed in the airflow control system 23 with a quick disconnect fitting 34. The inflow air channel 7 connects proximally to the quick detachable inflow air channel ports and channel caps 8 of the airflow liner 6, as depicted.

Pushbutton actuators 31 which open and close the electromechanical airflow proportioning mechanism 22 are located on the circuit control board housed in the airflow control system 23. The outflow air channel 25 connects proximally to the artificial limb socket 30 at the barb fitting 29 received by the four-bolt airflow lamination plate 15. The outflow air channel connects distally to the negative gauge pressure generating device housed in the airflow control system 23. A replaceable and/or rechargeable battery 53 powers the system.

When the electromechanical proportioning mechanism 22 is opened, an immediate pressure differential exists and air enters the system at point 24, which is the inlet side of an air filter connected inline with the electromechanical proportioning mechanism of the airflow initiating device. Air travels through the electromechanical proportioning mechanism 22 past the quick disconnect fitting 34, past the Y which divides the inlet air supply equally to the air flow channels 7 supplying the medial and lateral sides of the airflow liner 6, past the T 33 which divides the air supply equally again to the anterior and posterior quick detachable inflow air channel ports and channel caps 8 located on the proximal medial and proximal lateral sides of the airflow liner 6.

Air travels between the limb and airflow liner 6, through the surface are multiplying textile layer with airflow seal that defines the negative gauge pressure environment between the limb and airflow liner 6. Air travels over the amputee's stump, drawing away moisture, and past the distal air outflow channel port of the air flow liner 6, through the hollow locking suspension pin and into the four-bolt airflow lamination plate 15 of the prosthetic socket 30, moving towards the negative gauge pressure generating device housed in the airflow control system 23 via the outflow air channel 25. The negative gauge pressure generator functions to maintain secure adherence of the limb and liner creating and maintaining the pressure differential that draws regulated air into and through the system. Once the air passes through negative gauge pressure generator, air and moisture exhausts the system at point 27.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A negative gauge pressure moisture management and secure adherence artificial limb system to be attached to a residual limb of an amputee, the system comprising:

an artificial limb-conforming flexible airflow liner to be donned over the residual limb; and a surface area multiplying textile layer, including a proximal airflow seal, and to directly engage and surround at least a portion of the residual limb and define a regulated negative gauge pressure environment between the liner and the residual limb;

the liner having a plurality of airflow passageways therethrough and defining proximal inflow air channels and at least one distal outflow air channel in fluid communication with the regulated negative gauge pressure environment.

2. The negative gauge pressure moisture management and secure adherence system according to claim 1, wherein the artificial limb airflow liner includes detachable air inflow channel ports.

3. The negative gauge pressure moisture management and secure adherence system according to claim 2, wherein each of the detachable air inflow channel ports comprises an occlusion preventing airflow flange in fluid communication with the defined negative gauge pressure environment between the residual limb, the surface area multiplying textile layer, and airflow liner.

4. The negative gauge pressure moisture management and secure adherence system according to claim 3, wherein the occlusion preventing airflow flange includes a plurality of airflow holes in a circular pattern and feeding into a central inflow air channel and further into airflow grooves along a face of the flange.

5. The negative gauge pressure moisture management and secure adherence system according to claim 1, wherein the artificial limb airflow liner includes a distal air outflow channel port having an occlusion preventing airflow flange in fluid communication with the defined negative gauge pressure environment between the residual limb, the surface area multiplying textile layer, and airflow liner.

6. The negative gauge pressure moisture management and secure adherence system according to claim 5, wherein the occlusion preventing airflow flange of the distal air outflow channel has a plurality of airflow holes in a circular pattern and feeding into a central outflow air channel and further into airflow grooves along a face of the flange.

7. The negative gauge pressure moisture management and secure adherence system according to claim 1, further comprising an airflow control system connected to the outflow and inflow air channels.

8. The negative gauge pressure moisture management and secure adherence system according to claim 7, wherein the airflow control system includes an airflow regulation device connected to the outflow air channel.

9. The negative gauge pressure moisture management and secure adherence system according to claim 8, wherein the airflow regulation device includes an electric negative gauge pressure generating device and an associated control circuit.

10. The negative gauge pressure moisture management and secure adherence system according to claim 7, wherein the airflow control system further includes an airflow initiating device connected to the inflow air channels.

11. The negative gauge pressure moisture management and secure adherence system according to claim 10, wherein the airflow initiating device comprises an electromechanical airflow control proportioning mechanism and associated control circuit.

12. The negative gauge pressure moisture management and secure adherence system according to claim 11, wherein the airflow initiating device further includes a wireless link for controlling at least the electromechanical airflow control proportioning mechanism.

13. The negative gauge pressure moisture management and secure adherence system according to claim 7, wherein the airflow control system further comprises:

a battery to power the electric negative gauge pressure generating device and associated control circuit, and to power the electromechanical airflow proportioning mechanism and associated control circuit; and a housing carrying the battery, electric negative gauge pressure generating device and associated control circuit, and electromechanical airflow proportioning mechanism and associated control circuit.

14. A method of attaching an artificial limb and moisture management and secure adherence system to a residual limb, the method comprising:

providing a negative gauge pressure limb-conforming flexible airflow liner;

providing a surface area multiplying textile layer, including a proximal airflow seal, and to directly engage and surround at least a portion of the residual limb and define a regulated negative gauge pressure environment between the negative gauge pressure airflow liner and the residual limb;

providing the airflow liner with a plurality of airflow passageways therethrough defining proximal inflow air channels and at least one distal outflow air channel in fluid communication with the regulated negative gauge pressure environment; and providing an airflow control system connected inline with the outflow air channel and inflow air channels.

15. The method according to claim 14, wherein the artificial limb airflow liner includes detachable air inflow channel ports.

16. The method according to claim 15, wherein the detachable air channel ports comprise an occlusion preventing airflow flange in fluid communication with the defined negative gauge pressure environment between the residual limb, the surface area multiplying textile layer, and airflow liner.

17. The method according to claim 16, wherein the occlusion preventing airflow flange has a plurality of airflow holes in a circular pattern and feeding into a central inflow air channel and further into airflow grooves along a face of the flange.

18. The method according to claim 17, wherein the artificial limb airflow liner includes a distal air outflow channel port with an occlusion preventing airflow flange in fluid communication with the defined negative gauge pressure environment between the residual limb and airflow liner.

19. The method according to claim 18, wherein the occlusion preventing airflow flange of the distal air outflow channel port has a plurality of airflow holes in a circular pattern and feeding into a central outflow air channel and further into airflow grooves along a face of the flange.

20. The method according to claim 14, wherein the airflow control system includes an airflow regulation device connected to the outflow air channel.

21. The method according to claim 20, wherein the airflow regulation device includes an electric negative gauge pressure generating device and associated control circuit.

22. The method according to claim 14, wherein the airflow control system includes an airflow initiating device connected to the inflow air channels.

23. The method according to claim 22, wherein the airflow initiating device includes an electromechanical airflow proportioning mechanism and control circuit.

24. The method according to claim 23, wherein the airflow initiating device further includes a wireless link for controlling at least the electromechanical airflow proportioning mechanism.

25. The method according to claim 24, wherein the airflow control system further comprises:
- a battery to power the electric negative gauge pressure generating device and associated control circuit, and to power the electromechanical airflow proportioning mechanism and associated control circuit; and
- a housing carrying the battery, electric negative gauge pressure generating device and associated control circuit and electromechanical airflow proportioning mechanism and associated control circuit.

26. A negative gauge pressure moisture management and secure adherence artificial limb system to be attached to a residual limb of an amputee, the system comprising:
- an artificial limb airflow liner to be donned over the residual limb; and
- a surface area multiplying textile layer, including a proximal airflow seal, and to surround at least a portion of the residual limb and define a regulated negative gauge pressure environment between the liner and the residual limb;
- the liner having a plurality of airflow passageways therethrough and defining inflow air channels and at least one outflow air channel in fluid communication with the regulated negative gauge pressure environment;
- the liner including detachable air inflow channel ports each comprising an occlusion preventing airflow flange in fluid communication with the defined negative gauge pressure environment between the residual limb, the surface area multiplying textile layer, and airflow liner.

27. The negative gauge pressure moisture management and secure adherence system according to claim 26, wherein the occlusion preventing airflow flange includes a plurality of airflow holes in a circular pattern and feeding into a central inflow air channel and further into airflow grooves along a face of the flange.

28. A negative gauge pressure moisture management and secure adherence artificial limb system to be attached to a residual limb of an amputee, the system comprising:
- an artificial limb airflow liner to be donned over the residual limb; and
- a surface area multiplying textile layer, including a proximal airflow seal, and to surround at least a portion of the residual limb and define a regulated negative gauge pressure environment between the liner and the residual limb;
- the liner having a plurality of airflow passageways therethrough and defining inflow air channels and at least one outflow air channel in fluid communication with the regulated negative gauge pressure environment;
- the liner including a distal air outflow channel port having an occlusion preventing airflow flange in fluid communication with the defined negative gauge pressure environment between the residual limb, the surface area multiplying textile layer, and airflow liner.

29. The negative gauge pressure moisture management and secure adherence system according to claim 28, wherein the occlusion preventing airflow flange of the distal air outflow channel has a plurality of airflow holes in a circular pattern and feeding into a central outflow air channel and further into airflow grooves along a face of the flange.

* * * * *